(12) United States Patent
Stebbins et al.

(10) Patent No.: US 9,656,006 B2
(45) Date of Patent: May 23, 2017

(54) WEARABLE EXTERNAL VENTRICULAR DRAIN SYSTEM

(71) Applicant: Infinivation Biomedical, LLC, Lansing, NY (US)

(72) Inventors: Kristen Stebbins, Cicero, NY (US); Thomas J. Pennell, II, Moravia, NY (US)

(73) Assignee: InfinivationBiomedical, LLC, Moravia, NY (US)

( * ) Notice: Subject to any disclaimer, the term of this patent is extended or adjusted under 35 U.S.C. 154(b) by 75 days.

(21) Appl. No.: 14/057,705

(22) Filed: Oct. 18, 2013

(65) Prior Publication Data

US 2015/0112289 A1 Apr. 23, 2015

(51) Int. Cl.
*A61M 1/00* (2006.01)
*A61M 27/00* (2006.01)
(Continued)

(52) U.S. Cl.
CPC ........ *A61M 1/0035* (2014.02); *A61M 1/0021* (2013.01); *A61M 27/006* (2013.01);
(Continued)

(58) Field of Classification Search
CPC .............. A61M 1/0021; A61M 27/006; A61M 1/0035; A61M 2205/3523; A61M 2205/3561; A61M 2210/0693; A61M 2230/00; A61M 2209/088; A61M 2202/0464; A61M 2027/004; A61M 1/0019; A61M 2039/2473; A61M 2039/248; A61M 2039/2486; F16K 1/00; F16K 1/02; F16K 1/04; F16K 1/12; F16K 1/123; F16K 1/126; F16K 1/30; F16K 1/301; F16K 1/304; F16K 1/32; F16K 1/34; F16K 27/02; F16K 27/0209; F16K 15/063; F16K 1/38; F16K 1/385; F16K 1/2071; F16K 1/2266; F16K 1/307; F16K 17/04; F16K 17/06; F16K 27/0254; F16K 5/10; Y10T 137/7932; Y10T 137/7933;
(Continued)

(56) References Cited

U.S. PATENT DOCUMENTS 1,482,517 A * 2/1924 Kelsey .......................... 137/224
3,548,869 A * 12/1970 Anderson, Jr. ....... F16K 15/044
137/516.25
(Continued)

OTHER PUBLICATIONS

Woodbury; M. (US AI00142), May 6, 1856.*
(Continued)

*Primary Examiner* — Adam Marcetich
(74) *Attorney, Agent, or Firm* — Timothy W. Menasco, Esq.; Harter Secrest & Emery LLP

(57) ABSTRACT

A wearable EVD system having a ventricular catheter and transducer supported proximately to a patient's ear by a mount, such as supporting headband or ear clip. An adjustable orifice valve or a spring-loaded needle valve is used to control the amount of CSF that drains into a drip chamber suspended on the patient for periodic measurement and emptying into a similarly located drainage bag, thereby avoiding the need for an IV pole and allowing the patient more mobility without disrupting drainage of CSF.

9 Claims, 3 Drawing Sheets

(51) Int. Cl.
*F16K 15/06* (2006.01)
*F16K 17/04* (2006.01)
*F16K 1/20* (2006.01)
*F16K 1/38* (2006.01)
*F16K 5/10* (2006.01)

(52) U.S. Cl.
CPC ............ *A61M 2205/3523* (2013.01); *A61M 2205/3561* (2013.01); *A61M 2209/088* (2013.01); *A61M 2210/0693* (2013.01); *A61M 2230/00* (2013.01); *F16K 1/2071* (2013.01); *F16K 1/38* (2013.01); *F16K 5/10* (2013.01); *F16K 15/063* (2013.01); *F16K 17/04* (2013.01); *Y10T 137/7932* (2015.04); *Y10T 137/7935* (2015.04)

(58) Field of Classification Search
CPC ......... Y10T 137/7934; Y10T 137/7935; Y10T 137/7936
See application file for complete search history.

(56) References Cited

U.S. PATENT DOCUMENTS

| | | | | |
|---|---|---|---|---|
| 3,796,228 | A * | 3/1974 | Bedo | F16K 17/04 137/536 |
| 4,099,703 | A * | 7/1978 | Lush | 251/122 |
| 4,210,168 | A * | 7/1980 | Yonezawa | 137/454.5 |
| 4,402,340 | A * | 9/1983 | Lockwood, Jr. | F16K 1/305 137/322 |
| 4,500,311 | A * | 2/1985 | Redmond et al. | 604/246 |
| 4,568,499 | A * | 2/1986 | Wood | 261/41.5 |
| 4,766,927 | A * | 8/1988 | Conatser | F16K 1/42 137/315.13 |
| 4,858,619 | A * | 8/1989 | Toth | 600/561 |
| 5,176,175 | A * | 1/1993 | Farnham et al. | 137/614.18 |
| 5,234,420 | A * | 8/1993 | Horton | A61F 5/4408 224/663 |
| 5,772,625 | A * | 6/1998 | Krueger et al. | 604/9 |
| 5,776,105 | A * | 7/1998 | Corn | A61M 5/1483 604/174 |
| 6,561,480 | B1 * | 5/2003 | Komiya et al. | 251/129.12 |
| 7,285,296 | B2 | 10/2007 | Ginggen | |
| 7,922,685 | B2 | 4/2011 | Rosenberg | |
| 8,177,737 | B2 | 5/2012 | Negre et al. | |
| 8,282,566 | B2 | 10/2012 | Mauge et al. | |
| 8,298,168 | B2 | 10/2012 | Bertrand et al. | |
| 8,343,139 | B2 | 1/2013 | Ahmed | |
| 2002/0029406 | A1 * | 3/2002 | Meyer | A61M 25/02 2/310 |
| 2002/0087059 | A1 | 7/2002 | O'Keefe | |
| 2004/0102761 | A1 * | 5/2004 | Ahmed | 604/540 |
| 2005/0145809 | A1 * | 7/2005 | Lee | 251/83 |
| 2006/0052737 | A1 | 3/2006 | Bertrand et al. | |
| 2008/0294128 | A1 * | 11/2008 | Richards | A61M 27/00 604/327 |
| 2009/0005720 | A1 * | 1/2009 | Ludin et al. | 604/9 |
| 2010/0305493 | A1 | 12/2010 | Barr | |
| 2011/0071457 | A1 | 3/2011 | Raman | |
| 2011/0275976 | A1 | 11/2011 | Negre et al. | |
| 2011/0295615 | A1 * | 12/2011 | Bengtson | G06Q 50/22 705/2 |
| 2012/0226215 | A1 | 9/2012 | Hsu et al. | |
| 2012/0232461 | A1 | 9/2012 | Seaver et al. | |
| 2012/0232462 | A1 | 9/2012 | Miethke | |
| 2012/0253270 | A1 | 10/2012 | Steinbach | |
| 2012/0259265 | A1 | 10/2012 | Salchi et al. | |
| 2012/0302938 | A1 | 11/2012 | Browd et al. | |
| 2013/0023814 | A1 | 1/2013 | Bertrand et al. | |
| 2014/0194840 | A1 | 7/2014 | Eckermann | |

OTHER PUBLICATIONS

International Search Report Form PCT/ISA/220, International Application No. PCT/US2014/061137, pp. 1-12, Dated Mar. 12, 2015.

* cited by examiner

WEARABLE EXTERNAL VENTRICULAR DRAIN SYSTEM

BACKGROUND OF THE INVENTION

1. Field of the Invention

The present invention relates to external ventricular drain systems and, more particularly, to a wearable external ventricular drain system.

2. Description of the Related Art

Hydrocephalus is a medical condition characterized by an excess accumulation of fluid in the brain. It results in increased intracranial pressure ("ICP") and can cause severe brain damage or death if the pressure is not relieved. An external ventricular drain ("EVD") is used to drain excess cerebrospinal fluid ("CSF") in cases of temporary hydrocephalus such as brain hemorrhage and shunt malfunction in order to provide a therapeutic reduction in ICP.

The currently existing EVD system consists of a thin soft tube (ventricular catheter) that is inserted under sterile procedure into the ventricle of the brain. The distal end of the ventricular catheter is connected to the EVD tubing which leads to a drip chamber with an adjustable height that is mounted to a frame. This tubing is rigid in order to prevent damping of pressure pulsation coming from the brain. On the frame of the EVD are pressure markings and the system is leveled to the patient's ventricle at the level of zero pressure by adjusting the system height vertically to set the zero level of the system level with the patient's ventricles.

The drip chamber has volume markings to allow for recording of the amount of fluid collected per time increment (typically hourly) and is emptied into a larger bag using a three-way stopcock after the output has been recorded. The tubing between the ventricle and the drip chamber generally includes a port that can be used for sampling CSF. A three-way stopcock connects the tubing to the drip chamber so the drain can be closed off from draining entirely, or allow for pressure measurement without draining fluid.

A pressure transducer may be connected to the system before the drip chamber at the level of the patient's ventricle (zero pressure mark on the EVD) to measure the pressure in the brain when the drain is closed. The entire EVD system is mounted on an intravenous drip ("IV") pole where the EVD system can be raised and lowered as needed to maintain level with the ventricle. The pressure transducer is kept at a position that is level with the patient's ventricle and is connected to one branch of a three way stopcock. The reason for this connection is that the true pressure in the brain can only be measured when CSF flow is stopped (valve closed to drainage). The rigid tubing between the patient's brain and the pressure transducer does not affect the pressure reading, as it is an extension of the rigid cranial compartment. The transducer connects wirelessly or via cable to a monitor. The monitor generally displays an average ICP along with a pressure waveform. In the ICU setting, the nurse on call must be able to view an ICP waveform while draining CSF (valve open to pressure transducer, and to flow), or while the drain is closed.

The greatest issue with the current EVD system is that the zero level of the drain must be level with the patient's ventricle at all times. If the drain is not level with the patient's ventricle, more or less back pressure will be applied to the brain, and thus more or less CSF than desired will flow into the drip chamber. This requirement causes decreased safety to the patient and increased nursing time necessary to level the drain, as patients are prone to frequently adjusting the positions and elevations of their heads.

For example, many ICU patients with hydrocephalus have neurological deficits and cannot always remember that they have an EVD. These patients are likely to sit up quickly, which results in over-drainage of CSF into the EVD. Over-drainage can be very hazardous to the patient, possibly causing increased headache, collapse of ventricles, decreased cerebral perfusion, hemorrhage, and death. In addition, if the patient adjusts his/her bed from an elevated position to a horizontal position, under-drainage of CSF would occur. Under-drainage of CSF can lead to a dangerous over-accumulation of fluid in the brain, possibly causing headaches, nausea, brain damage, brain herniation, and death.

Conventional EVD systems thus result in decreased mobility and independence for ICU patients, which lead to poorer outcomes and loss of function while the patients are hospitalized. Brain bleeds and shunt infections may require the patient to be tethered to an EVD for a period of weeks. Each EVD patient must be closely visually monitored so that that the nurse can intervene as soon as the patient moves. Mobile ICU patients must ring their call bells each time they want to move so that the nurses can close and readjust the height of their EVD systems in order to maintain the zero levels of their EVDs relative to the patients' ventricles. Only properly trained nurses can adjust the EVD drain, so this requirement prevents other health care workers or family members from being able to assist the patients to reposition their heads, or move about the room or hospital.

Additionally, as a patient recovers, the patient's treatment may include physical therapy, which requires the patient to leave the bed. The patient or nurse then must bring the EVD, which is attached to an IV pole, and its lengthy tubing along with the patient. This procedure adds the risk of the patient tripping, and limits the amount of time that the patient can be out of the bed, since the EVD must be adjusted or turned off and closely monitored in order for the patient to stand.

BRIEF SUMMARY OF THE INVENTION

It is therefore a principal object and advantage of the present invention to provide an EVD system that results in increased mobility and independence for ICU patients, thus leading to better outcomes and increases of function while the patients are hospitalized.

In accordance with the foregoing objects and advantages, the present invention comprises a wearable EVD system having a ventricular catheter that is placed in the ventricle of the brain to drain CSF and a valve located in line with the patient's ear. A transducer may be also provided level with the patient's ventricle and connected to a monitor that continuously or periodically measures the intracranial pressure. The valve and transducer are firmly secured at the level of the ventricle with a support headband and/or ear clip. The valve may be either an adjustable orifice valve or a spring-loaded needle valve or any other adjustable valve. CSF that drains through the valve is collected in the drip chamber for periodic measurement and then emptied into the drainage bag. In a simpler embodiment, the CSF can collect directly into the drainage bag and the drip chamber may be left out. The drip chamber and drainage may be attached to the patient inferior to the cranium via securement straps. As a result, no IV pole is needed and a patient is free to sit up or move about while the EVD system is in place without disrupting drainage of CSF, eliminating the potential for patient harm.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
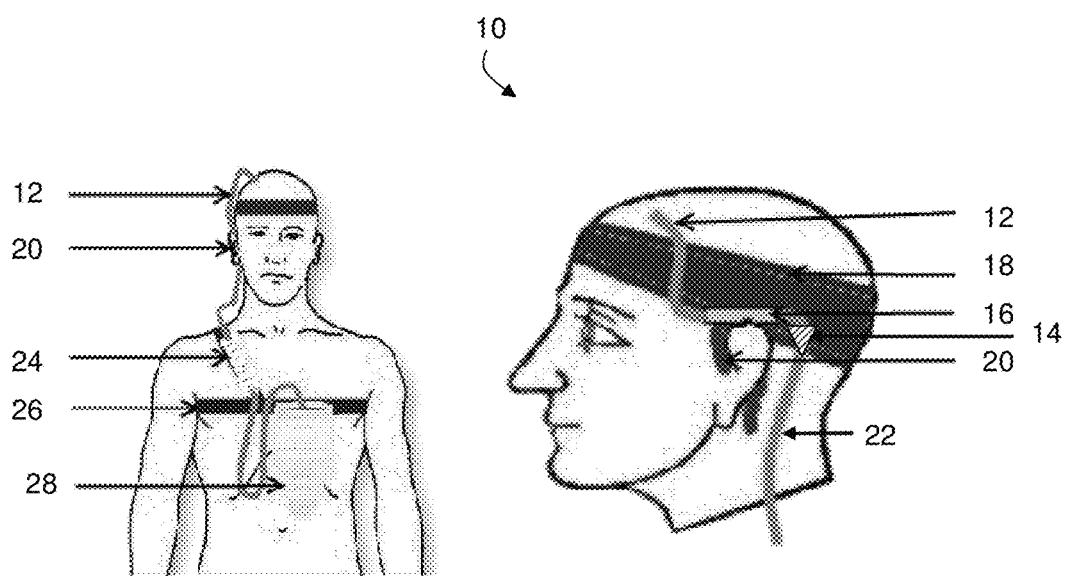
FIG. 1 is a schematic of a wearable external ventricular drain system according to the present invention.

Referring now to the drawings, wherein like reference numbers refer to like parts throughout, there is seen in FIG. 1 a wearable EVD system 10 comprising a ventricular catheter 12 that is placed in the ventricle of the brain to drain CSF. The amount of CSF drained is determined by a valve 14 which must be located at the level of the patient's ventricle. A transducer 16 may also be provided in this location and connected to a monitor that continuously measures the intracranial pressure. Alternatively, various other sensors may be used, such as a flow sensor or a glucose sensor, and or combinations thereof. Valve 14 and transducer 16 are firmly secured at the level of the ventricle with a support headband 18 and/or an ear clip 20. The headband and ear clip can be used independently, though used together provide the most secure fastening device. Head band 18 and/or ear clip 20, which may be flexible, hold the valve 14, and optionally, pressure transducer 16 and an array of sensors conducting measurements on the CSF at the level of the patient's ventricle.

Valve 14 is preferably an adjustable orifice valve or a spring-loaded needle valve as exampled in more detail below. CSF that drains through valve 14 is passed through drain tubing 22 and optionally collected in a drip chamber 24 which is attached via a removable connector (such as hook and loop, or a pocket) to the front of a securement strap 26. The collection of fluid in drip chamber 24 may be periodically measured and then emptied into a drainage bag 28 via a three-way stopcock (not shown). Drainage bag 28 is attached to a horizontal portion of securement strap 26 also using a removable connection so that the drainage bag can be changed when full. The securement strap 26 is adjustable and can be easily removed or adjusted to fit patients of any size. Drainage bag 28 can optionally be hung on the side of a bed when the patient is in bed or it may be attached to a patient, such as by a securement strap, when the patient is mobile.

Proposed wearable EVD system 10 thus relocates the system from the IV pole and attaches the system to the patient. Transducer 16 and drain tubing 22 is attached to the head of a patient at the same level as the ventricles within the brain. System 10 thus allows the patient to move as he/she pleases (within the constraint placed by the length of the cable extending from the pressure transducer, if used) without the risk of over or under draining CSF through system 10. Transducer 16 may be provided with wireless capabilities to interface with a remote monitoring system or attached via a data line. For example, some existing ICU monitors are wireless and thus transducer 16 could be wireless to interface with this system. Regardless, a patient may be untethered from a monitor.

Valve 14 is preferably adjustable to control the flow of CSF from the patient's ventricles, which is a departure from conventional EVD systems that use hydrostatic pressure to create back pressure on the flow of the CSF from the ventricle so that when the drain is raised, the ICP must overcome the hydrostatic pressure of the drain before CSF flow will occur. System 10 includes an adjustable valve 14 that may be located on or near the ear piece and/or headband to provide the necessary back pressure, which may be adjusted based on a physician's orders. Valve 14 thus provides the necessary back pressure to the patient's ventricles, which will properly regulate drainage. Valve 14 may include a check valve portion, in the needle valve embodiment discussed below, to prevent retrograde flow into the brain. By contrast, an orifice type version of valve 14 would provide restriction to retrograde flow based on its setting and would minimize the effect of retrograde flow of CSF to the ventricles.

Figure 2:
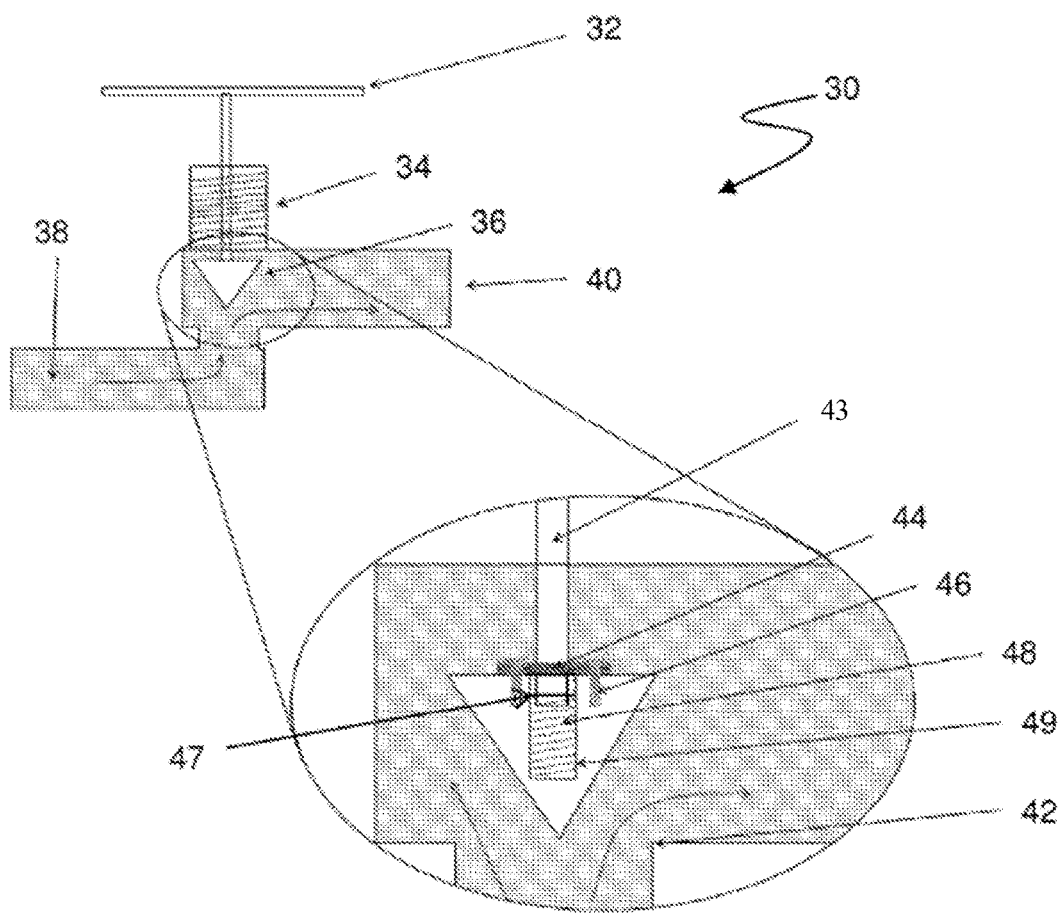
FIG. 2 is a schematic of an adjustable needle valve for a wearable external ventricular drain system according to the present invention.

The present invention encompasses at least three embodiments for valve 14, although one or more alternative valves may be employed instead. As seen in FIG. 2, the first embodiment of valve 14 is an adjustable, spring-loaded needle valve. Needle valves are capable of sensitive adjustments and high degrees of attainable resolution. This high resolution is critical, since using the device necessitates operating within a small pressure range. A needle valve according to the present invention is preferably adjustable from 0-30 mmHg in increments of 1 mmHg. Needle valve 30 comprises an adjustment knob 32 having advancement threads 34 for advancing or retracting a needle in the flow path having a fluid inlet 38 and a fluid outlet 40. As further seen in FIG. 2, needle 36 is adapted to engage a needle seat 42 positioned between fluid inlet 38 and fluid outlet 40, thereby adjusting the amount of fluid that can flow from fluid inlet 38 to fluid outlet 40. When needle 36 is positioned far away from needle seat 42, there will be little to no back pressure toward fluid inlet 38. As needle 36 approaches needle seat 42, there will be greater back pressure created by the flow restriction. Once the needle is in contact with the seat, the ICP must overcome the adjustable spring force in order to open the valve. Needle 26 can have either a flat, rounded, or a tapered bottom, although a tapered bottom allows for more surface area and provides for a finer adjustment due to increased surface area.

In a further embodiment of a needle style valve, needle 36 may comprise an adjustment rod 43 that is interconnected to needle 36 via a retainer clip 44 and retainer screw 46. Adjustment rod 43 is further interconnected to needle 36 and a spring 48 positioned within a housing 49 that abuts against a compression plate 47 positioned along rod 43. By rotating adjustment knob 32, needle 36 is advanced or retracted and held in position by needle advancement threads 34. Needle 36 may be advanced toward needle seat 42 in order to provide some back pressure toward fluid inlet 38. When engaged, spring 48 makes adjustment of the back pressure more sensitive by exerting a known force on the needle toward the needle seat. Any fluid passing into the inlet will have to overcome this force to lift needle 36 against the bias of spring 48 in order to pass through the fluid outlet.

The second embodiment of valve 14 comprises an orifice valve 50 that is adjustable both in diameter and length. The back pressure provided by an orifice is provided by both its diameter and its length according to the Hagen-Poiseuille equation:

$$\Delta P = \frac{8\mu L Q}{\pi r^4}$$

Figure 3:
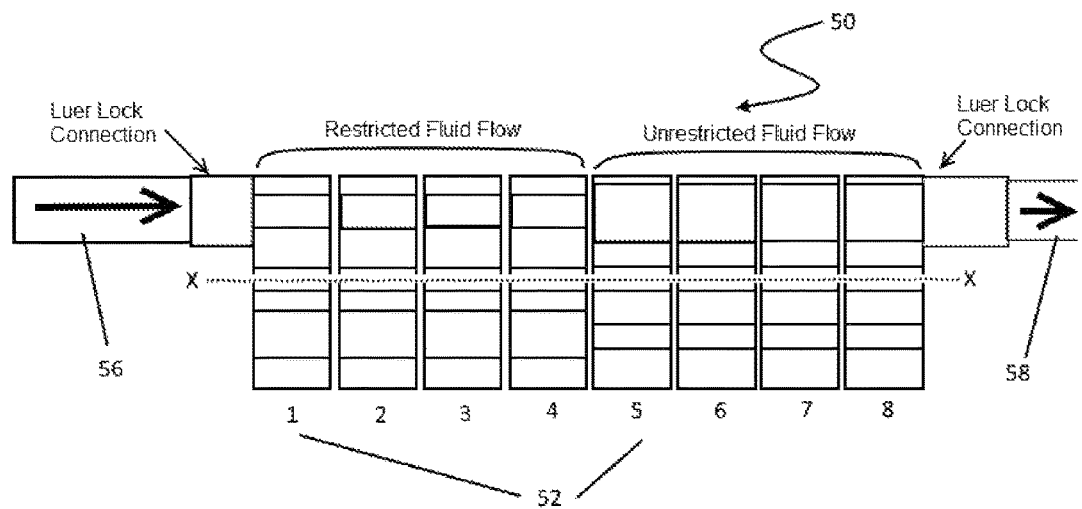
FIG. 3 is a schematic of an adjustable orifice valve for a wearable external ventricular drain system according to the present invention.
Figure 4:
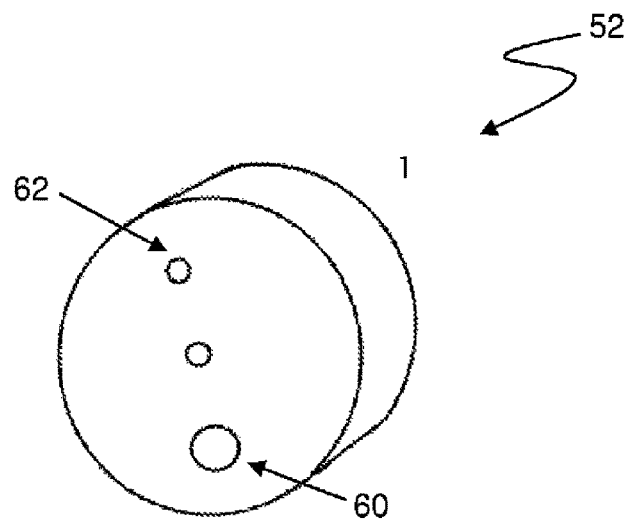
FIG. 4 illustrates a cylinder of an exemplary orifice valve.

As seen in FIG. 3, a series of rotating cylinders 52, each having multiple orifices of varying diameters, are aligned along a common axis X-X. Orifices are preferably offset from the axis of rotation and positioned to align with a fluid pathway by a fluid input tube 56 to a fluid outlet 58. As seen in FIG. 4, each cylinder 52 has a small orifice 60 and large orifice 62 that may be selectively aligned along fluid pathway and configures to provide a certain back pressure according to the Hagen-Poiseuille equation. For example, aligning the small orifices 62 of four cylinders 52, each providing 1 mmHg back pressure, with the large orifices 62 of four remaining cylinders 52, will provide a total of 4 mmHg back pressure. Each cylinder 52 may be sealed against adjacent cylinders 52 to provide a continuous, leak proof fluid path. For example, o-rings or gaskets may be used provided that they are employed in a manner that would not obstruct fluid flow or disengage within the fluid path.

In a third embodiment, valve 14 may comprise an array of orifices of various specific diameters and lengths that provide a range of back pressures according to the Hagen-Poiseuille equation. A moveable shutter that selectively exposes a predetermined single orifice or array of orifices may be used to allow a user to adjust the specific amount of back pressure for system 10.

What is claimed is:

1. A wearable external ventricular drain system, comprising
    a ventricular catheter;
    a head mount adapted to releasably engage a head of a patient;
    a valve engaged with the head mount to locate the valve in proximity of a ventricle of the patient, the valve having an input interconnected to the ventricular catheter and an output, a fluid passageway connecting the input and the output, a needle seat positioned in the passageway, an adjustable needle having a needle head positioned in the fluid passageway for movement into and out of engagement with the needle seat, a post interconnected at one end to the needle head and to a knob at the opposing end, wherein the post is interconnected to the needle head via a spring and wherein the needle head with the spring is operable to move relative the needle seat to allow a flow of fluid from the input to the output;
    a drain line interconnected to the output of the valve;
    a securement strap adapted to engage one of a chest and a shoulder of the patient;
    a drip chamber fluidly connected to the drain line and engaged with the securement strap, the drip chamber operable to provide a visual measure of a collection of the flow of fluid; and
    a reservoir interconnected to the drainage tubing downstream of the drip chamber.

2. The system of claim 1, further comprising at least one sensor interconnected to the catheter and the mount.

3. The system of claim 2, wherein the sensor is selected from the group consisting of a pressure transducer, a flow sensor, and a glucose sensor, and combinations thereof.

4. The system of claim 2, wherein the sensor is adapted to wirelessly transmit data to a remotely positioned host.

5. The system of claim 2, wherein the sensor is electrically interconnected to a remotely positioned host and transmits data to the host.

6. The system of claim 1, further comprising a stopcock interconnected to the drip chamber for emptying of the drip chamber.

7. The system of claim 6, further comprising drainage tubing interconnected to the stopcock and in fluid communication with the drip chamber when the stopcock is in an open position.

8. The system of claim 1, further comprising a reservoir interconnected to the drain line, the reservoir engaged with the securement strap.

9. A valve for an external ventricular drain system, comprising:
    a fluid passageway having an input and an output, the input fluidly connected to a ventricular catheter;
    a needle seat positioned in the passageway around the input;
    an adjustable needle having a needle head positioned in the fluid passageway over the input for movement into and out of engagement with the needle seat;
    a post interconnected at one end to the needle head and to a knob at the opposing end, wherein the post is interconnected to the needle head via a spring;
    a head mount to locate the valve in proximity of a ventricle of a patient; and
    a drip chamber fluidly connect to the fluid passageway, the drip chamber coupled to a securement strap adapted to engage one of a chest and a shoulder of the patient, the drip chamber operable to provide a visual measure of a collection of the flow of fluid, and wherein the needle head with the spring is operable to move relative the needle seat to allow a flow of fluid from the input to the output.

* * * * *

UNITED STATES PATENT AND TRADEMARK OFFICE
CERTIFICATE OF CORRECTION

| | | |
|---|---|---|
| PATENT NO. | : 9,656,006 B2 | Page 1 of 1 |
| APPLICATION NO. | : 14/057705 | |
| DATED | : May 23, 2017 | |
| INVENTOR(S) | : Kristen Stebbins and Thomas J. Pennell, II | |

It is certified that error appears in the above-identified patent and that said Letters Patent is hereby corrected as shown below:

On the Title Page

The Assignee name should read:
--Infinivation Biomedical, LLC--.

Signed and Sealed this
Eighth Day of August, 2017

Joseph Matal
*Performing the Functions and Duties of the*
*Under Secretary of Commerce for Intellectual Property and*
*Director of the United States Patent and Trademark Office*